United States Patent [19]
Altshuler et al.

[11] Patent Number: 5,259,391
[45] Date of Patent: Nov. 9, 1993

[54] METHOD AND DEVICE FOR CELL SAMPLING

[76] Inventors: John H. Altshuler, 5700 Dunbarton Dr., Englewood, Colo. 80111; David T. Altshuler; Sharman B. Altshuler, both of RD 1, Box 1160, Rupert, Vt. 05768

[21] Appl. No.: 709,692

[22] Filed: Jun. 3, 1991

[51] Int. Cl.⁵ ............................................. A61B 10/00
[52] U.S. Cl. ................................................... 128/759
[58] Field of Search ........................ 128/749, 756, 759

[56] References Cited

U.S. PATENT DOCUMENTS

| | | | |
|---|---|---|---|
| 4,127,113 | 11/1978 | Nollan | 128/756 |
| 4,221,225 | 9/1980 | Sloan | 128/750 |
| 4,523,278 | 6/1985 | Reinhardt et al. | 364/413 |
| 4,620,548 | 11/1986 | Hasselbrack | 128/758 |
| 4,754,764 | 7/1988 | Bayne | 128/756 |
| 4,762,133 | 8/1988 | Bayne et al. | 128/756 |
| 4,873,992 | 10/1989 | Bayne | 128/756 |
| 4,877,037 | 10/1989 | Ko et al. | 128/759 |
| 4,978,504 | 12/1990 | Nason | 128/759 |
| 5,031,635 | 7/1991 | Koll | 128/759 |

FOREIGN PATENT DOCUMENTS

| | | | |
|---|---|---|---|
| 2513941 | 9/1976 | Fed. Rep. of Germany | 128/759 |
| 2599500 | 12/1987 | France | 128/759 |

OTHER PUBLICATIONS

Vooijs, et al., Acta Cytologica, vol. 30, pp. 251–257, 1986.
Koprowska, et al., Acta Cytologica, vol. 30, pp. 207–212, 1986.
Tseng, et al., Ophthalmology, vol. 92, pp. 728–733, 1985.
Rubio, et al., Obstetrics and Gynecology, vol. 49, pp. 576–579, 1977.
Nelson, et al., Arch. Ophthalmol., vol. 101, pp. 1869–1872, Dec. 1983.

Primary Examiner—Max Hindenburg
Attorney, Agent, or Firm—Banner, Birch, McKie & Beckett

[57] ABSTRACT

A method and device are disclosed for sampling cells of the human female reproductive tract. According to the method, cells can be collected and observed on the same surface. The device comprises a cell collection substrate and a support member to hold the substrate, and optionally a grasping member.

23 Claims, 3 Drawing Sheets

FIG. 5A
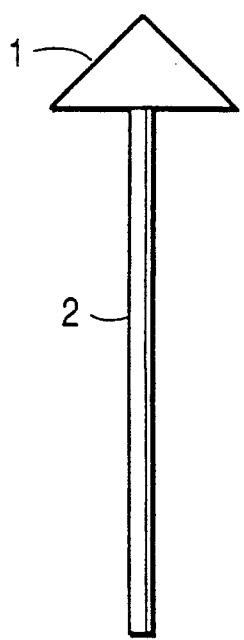
FIG. 5B
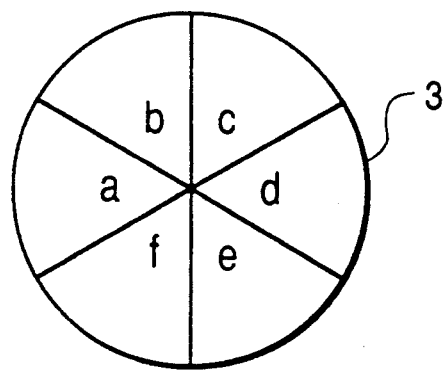
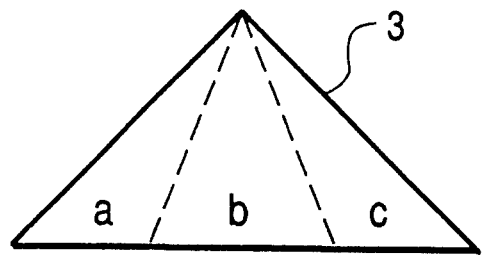
FIG. 5C

METHOD AND DEVICE FOR CELL SAMPLING

TECHNICAL FIELD OF THE INVENTION

This invention relates to sampling of the female reproductive system for the detection of disease.

BACKGROUND OF THE INVENTION

In the early 1940s, Dr. Papanicalou developed a technique whereby cells from the uterine cervix could be sampled with a cotton swab, placed on a glass slide, stained and examined for evidence of malignant change. The technique was named after him and has been referred to as the "PAP" smear. In the last fifty years the PAP smear has been used as a screening test for cancer. In addition, during the last fifteen years many refinements of this procedure have been developed, so that it is no longer used exclusively for cancer detection but is now also used to diagnose sexually transmitted diseases, to determine hormonal function, and to assess the possibility of threatened abortion. The accuracy of results obtained in a "PAP" smear is dependent on three variable: (1) the sample taken; (2) the laboratory procedure for processing and preparing the sample for interpretation; and (3) the accuracy of the interpretation of the prepared and processed sample. Of the three variables, errors in the sample taken appear to have the largest effect on the accuracy of results.

The collection of samples for PAP smears is usually done by a physician or a trained practitioner. The sample is taken through a speculum which is inserted into the vaginal opening. Samples are best taken from the transformation zone of the cervix. This zone is the area of change in the type of cells that line the cervix and this area most frequently reveals the development of cancer. Many methods for sampling the transformation zone have been devised. Current procedures employ cotton swabs, wood spatulas, and nylon brushes. However, these devices are less than fully satisfactory because they do not provide a fully representative sample of transformation zone cells.

Impression cytology is a procedure in which a filter is placed in contact with a tissue surface and then removed. When the filter is removed a thin layer of cells typically adheres to the filter. The filter and adherent cells are then processed and examined microscopically for diagnostic purposes. This technique has been used for diagnosis of a variety of eye conditions, such as blepharoconjunctivitis, keratoconjunctivitis sicca, and primary ocular surface disease. (Nelson, et al., *Archives Ophthalmology*, vol. 101, pp. 1869-1872, 1983.) The technique of impression cytology has also been applied to the examination of tissues which have been surgically removed, for example, cervical tumors and hysterectomy specimens, and biopsies. (Koprowska, et al., *Acta Cytologica*, vol. 30, pp. 207-212, 1986.) The present invention applies the technique of impression cytology to the sampling of cells from the human female reproductive tract.

SUMMARY OF THE INVENTION

It is an object of the invention to provide a device for sampling cells of the human female reproductive tract.

It is another object of the invention to provide a method for obtaining cell samples suitable for microscopic examination from a human female reproductive tract.

These and other objects of the invention are provided by one or more of the embodiments described below. In one embodiment of the invention a device is provided for obtaining cell samples suitable for microscopic examination directly from a human female reproductive tract, comprising: a cell collection substrate for adhering cells; a support member for holding said cell collection substrate; and a grasping member.

In another embodiment a method is provided of obtaining cell samples suitable for microscopic examination directly from a human female reproductive tract, comprising: contacting a human female reproductive tract with a cell collection substrate held by a support member to adhere cells from the human female reproductive tract to the cell collection substrate; and fixing the cells which adhere to the cell collection substrate on the cell collection substrate.

The methods and devices of the present invention provide a sensitive and accurate way to assess cytological changes related to neoplasm and infection. Ideal preparations for cytological observation consist of cells which are evenly deposited over the slide with minimal overlap. (Hurley et al, American Clinical Laboratory, April 1991, page 21.) The present invention more closely approaches this goal than prior sampling techniques and devices. Therefore, clearer observation and optimal diagnostic accuracy are provided by the present invention.

BRIEF DESCRIPTION OF THE DRAWINGS

FIG. 1 schematically shows a cell collection device with a conical support member (1) for holding membranes. The angle and diameter of the conical portion can vary, as shown.

FIG. 5A depicts a side view of a cell collection device which has a conical support member (1) and a straight grasping means (2). The top view (FIG. 5B) shows the cell collection membrane (3) which is impregnated with six different selective binding agents, a-f. FIG. 5C shows a side view of the cell collection membrane as installed on the conical support member (1).

DETAILED DESCRIPTION

Figure 1A:
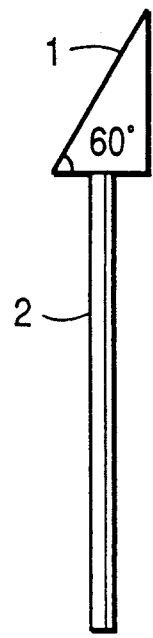
In FIG. 1A the angle at the base of the conical portion is 60 degrees.

It is a discovery of the present invention that the technique of impression cytology can be successfully and advantageously applied to collecting samples in situ from the human female reproductive tract. According to the present invention a cell collection substrate, such as a synthetic membrane, is contacted with the target cells of the body in situ. No biopsy or surgical removal is required. The target cells which adhere to the cell collection substrate are immediately fixed on the substrate. Thereafter the substrate with adhered cells can be stored or transported for analysis.

For analyzing the sample for cytological features, typically a staining procedure will be employed. Any staining procedure known in the art can be used. The substrate can be removed from a support member and adhered to a microscope slide. The substrate then is treated to render it transparent to visible light. The collected cells then are observed under a microscope by a cytologist or pathologist.

The cell collection substrate can comprise any material to which cells will adhere and which can be rendered transparent to the light used to illuminate a microscope slide. These lights include visible light, ultraviolet light, infrared light, etc. Such materials include polycarbonate membranes, cellulose acetate membranes, nitrocellulose membranes and glass fiber membranes. Other papers, plastics, and glasses can also be used.

In one embodiment of the invention the cell collection substrate is impregnated with a selective binding agent, such as an antibody, antigen, or lectin. Using such impregnated cell collection substrate the cell samples can be subjected to immunochemical techniques. For example, the cell collection substrate can be subjected to wash conditions prior to fixation such that only cells bound by a specific binding agent remain adhered. Detection of remaining adhered cells is then diagnostic for a particular pathogen, for example. Particular antibodies which may be desirably used are those specific for papilloma virus or chlamydia. Particular examples of antigens which may be used are tissue antigens, transplantation antigens and blood group antigens. Particular lectins which may be desirably used are *Arachis hypogaea, Anguilla anguilla, Dolichos biflorus, Cepaea nemoralis, Lotus tetragonolobus, Iberis amara, Ulex europaeus, Vicia cracca* or *cretica* or *graminea, Helix hortensis, Bauhinia purpurea* or *variegata, Ricinus communis, Molluccella laevis, Glycine soja, Fomes fomentarius, Saliva sclarea* or *horminum* and *Leonuras cardiaca*. Other reasons or modes for using a selective binding agent are selective identification of natural or acquired proteins on the surfaces of biologic tissues. Furthermore, selective binding agents embedded in the membrane may be applied to a mucosal surface for purposes of inducing host antibody responses. The induced antibody response may be a primary or secondary immune response to protect the host against infection from various organisms. Such application allows the agent to become exposed to the circulatory system because of the rich vascularity of the transformation cervical-endocervical region. An example of such induced protection is the application of small pox vaccine to the skin and subsequent scarification allowing vaccine to be exposed to the circulation.

A support member (element (1) in FIGS. 1A, 1B, 2A, 2B, 3, 4, and 5A) holds the cell collection substrate (element (3) in FIGS. 5B and 5C). Typically it is made of a rigid plastic material. Other materials can also be used, such as wood, metal, cardboard, etc. Principally, the support member provides a means for manipulating the cell collection substrate without having to handle it with human hands. In addition, it allows the cell collection substrate to retain a particular geometric conformation, so that two points on the cell collection substrate maintain a constant distance between them throughout the cell collection process. Thus the relative position of the cells on the cell collection substrate may better reflect the relative positions which they occupied in the body.

The support member holds the cell collection substrate by any means which will achieve the goal of keeping all points on the cell collection substrate in a fixed spatial orientation with respect to each other. The cell collection substrate can be attached using an adhesive, such as glue or tape, or it can be fitted into grooves in the support member or it can be clipped or clamped to the support member. Other methods of attachment will readily occur to those of skill in the art, and these are encompassed by the present invention also.

The cell collection substrate can remain attached to the supporting member during all steps of sample processing up until microscope slide mounting. Alternatively, the cell collection substrate can be separated or removed from the rest of the device prior to or during any step of sample processing.

Figure 1B:
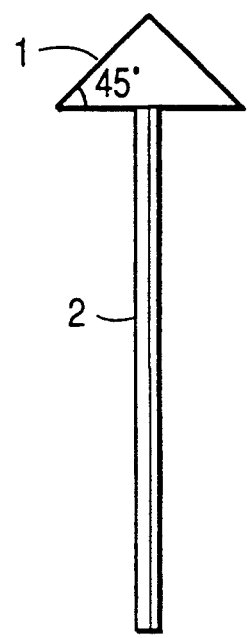
In FIG. 1B the angle at the base of the conical support member is 45 degrees.
Figure 1C:
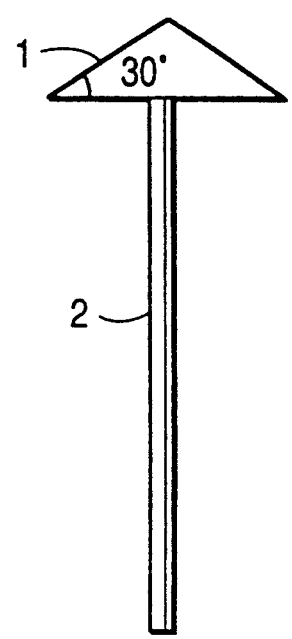
In FIG. 1C the angle at the base of the conical support member is 30 degrees. The optional grasping member (2) is substantially straight, and centered with respect to the conical support member.
Figure 2A:
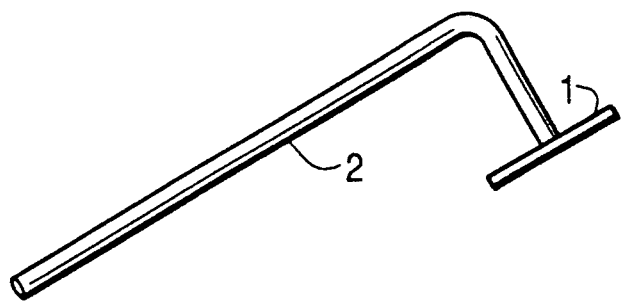
FIG. 2A depicts a side view of a cell collection device which has a flat portion (1) to support membranes. The grasping member (2) is substantially straight with an elbow.
Figure 3:
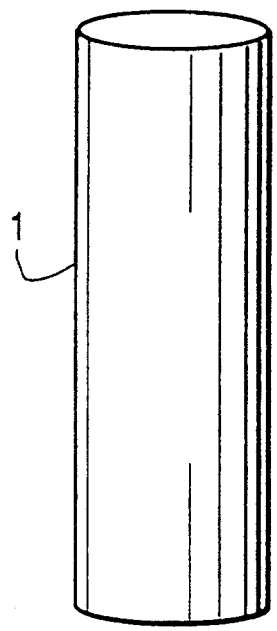
FIG. 3 shows a cell collection device wherein the support member (1) is curved. The support member also serves as a grasping member.

The grasping member (element (2) in FIGS. 1A, 1B, 1C, 2A, 4, and 5A) can be made out of the same material as the supporting member or a different material. It may be one continuous piece of the supporting member or it may be a separate piece attached thereto. In one embodiment of the invention the grasping member is merely a portion of the supporting member which a sample-collecting or sample-processing person can grasp, as shown in FIG. 3, element (1). The grasping member can be held by a person's hand directly or via a tool or implement such as a clamp. The grasping member is useful both during the sample collection and sample processing phases, although it is not critical that it remain attached to the supporting member through all processing steps.

Figure 2B:
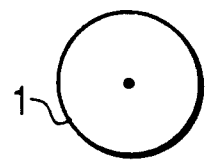
FIG. 2B shows a top view of the flat portion (1) to support membranes.

In a preferred embodiment of the invention the support member comprises a conical portion for holding the cell collection substrate. One such device is shown in FIG. 1. The angle at the base of the cone (see FIG. 1) can vary from about 30° to about 75°, the diameter of the cone decreasing accordingly. FIG. 1A shows a device with an angle at the base of the cone of 60 degrees. FIG. 1B shows a device with an angle at the base of the cone of 45 degrees. FIG. 1C shows a device with an angle at the base of the cone of 30 degrees. Thus sizes and shapes can be chosen to fit with various anatomical locations and with the varying sizes of anatomical parts found in the patient population. The conical shape is preferred for sampling the cervicalendocervical transformation zone of the uterine cervix. (See also FIG. 5A) However, for other anatomical locations other conformations may be desirable. The support member may be cylindrical (as in FIG. 3), flat (as in FIGS. 2A and 2B, showing side and top views, respectively) or curved (as in FIG. 4, element (1)), for example.

In one embodiment of the invention immunohistochemical reagents can be used to stain or counterstain the collected cells. This can provide additional diagnostic information to the pathologist, in addition to morphological observations. For example, tumor-specific or -associated antigens can be stained using antibodies which are specific for them. The presence of such antigens in conjunction with cytological observations can provide staging information, for example, regarding the progression of the neoplasia. (Specific examples of the use of immunohistochemical reagents include the demonstration of certain ABO blood group antigens in normal cervical epithelium. Progressive loss of these antigens on cervical epithelium occurs as the epithelium undergoes atypical changes. When the cervical mucosa becomes malignant, certain ABO blood group antigens which are normally present are not detectable by traditional immunological testing procedures.) Antibodies specific for pathogenic organisms' antigens can also be used as immunohistochemical reagents. For example, cytomegalovirus (CMV) infects cells of the human female reproductive tract. Thus anti-CMV antibodies can be used diagnostically as an immunohistochemical reagent.

In one embodiment of the invention a plurality of different specific binding agents are impregnated onto the cell collection substrate or membrane. These are positioned at predetermined locations. See FIGS. 5B and 5C for an example of the positioning of the different binding agents. One cell collection substrate thus can be used as a diagnostic tool for a plurality of antigens or pathogens.

The step of adhering the cell collection substrate to a microscope slide can be accomplished by allowing a wetted substrate to dry onto the slide. Alternatively, a number of adhesives can be used. One part adhesives which can be used include 3M Repositionable Adhesive 75, which comprises 1,1,1-trichloroethane, isobutane, nonvolatile components and 1,4-dioxane; 3M 4475 Plastic adhesive, a methyl ethyl ketone glue; 3M Pronto CA7 Instant Adhesive, a methyl cyanoacrylate glue; and Permabond 9WFS adhesive, an alpha cyanoacrylate ester. A two-part adhesive which can be used in Shell Chemical's Epon 828 & C.A.D. Pressure-sensitive adhesives which can be used include, 3M ATG 100 Adhesive Applicator loaded with 3M Scotch 924 Adhesive transfer tape, Lepage's Miracle Tape and Lepage's transparent tape.

A variety of cell fixatives are known in the art for cytological use and any of these may be used. These include but are not limited to ethyl alcohol, and Cytoprep TM (an alcohol-based cell fixative from Baxter Scientific). A variety of treatments can be employed to render the cell collection substrate optically transparent, and these can be chosen according to the material used for the cell collection substrate to achieve the optimum results. For nitrocellulose substrates, chloroform can be used. For polycarbonate substrates, cellulose acetate substrates, and glass fiber substrates numerous organic solvents may be used to render the background transparent. Examples of such solvents include xylene, benzene, ethyl acetate, Clearium TM (Surgipath Corp.), and petroleum ether.

EXAMPLES

EXAMPLE 1

Production of Cell Sampling Device

Figure 4:
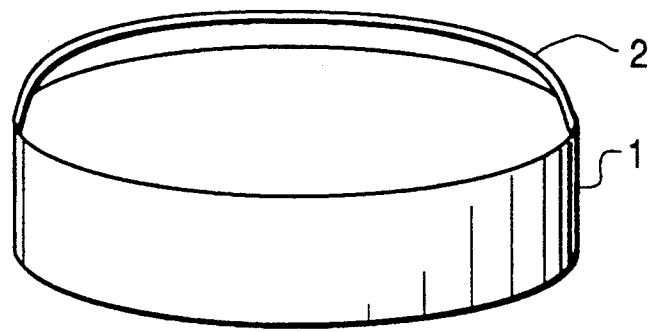
FIG. 4 shows a cell collection device wherein the support member (1) is curved and the grasping member (2) is distinct from the support member.

A clean, rigid plastic is machine lathed according to the specifications shown in the Figures. Individual parts, such as the support member and the grasping member shown in FIGS. 1, 2, and 4 are glued together. Membrane is cut to the appropriate size and shape using free-hand scissor technique or using a template. Rubber gloves are used when handling the membrane to avoid contamination. The cut membrane is adhered to the support member using tape. The device is packaged in a clean bag. Sterility is not required.

EXAMPLE 2

Use of Cell Sampling Device to Obtain All Samples

A physician or another trained professional dilates the patient's vagina by means of a speculum and removes the cell sampling device from its packaging. The exposed surface of the nitrocellulose membrane cell collection substrate is firmly pressed to the transformation zone for a short period of time, typically less than 3 seconds, but in some cases for more than 30 seconds. (Shorter exposure times are used for sampling gynecologic tissues using non-impregnated membranes. Longer times may be required for immunochemical techniques or for inducing host antibody responses.) The cell sampling device is removed from the vagina.

The surface of the nitrocellulose membrane which has been exposed to the transformation zone is placed in a 95% solution of ethyl or isopropyl alcohol. The preserved specimen can be stored for up to 12 months, or immediately transported to a cytology or pathology laboratory.

EXAMPLE 3

Processing of the Collected Samples

The exposed nitrocellulose membrane, still attached to the cell collection device, is immersed sequentially in the following reagent baths for the indicated time:
95% ethyl alcohol for 15 minutes
Room temperature tap water for 1 minute
Cold tap water for 1 minute
Hematoxylin for 1 minute
Scott's tap water (wetting agent) for 1 minute
Room temperature tap water for 1 minute
Room temperature tap water for 1 minute
95% ethyl alcohol for 30 seconds
95% ethyl alcohol for 30 seconds
Orange G stain for 1 minute
95% ethyl alcohol for 30 seconds
95% ethyl alcohol for 30 seconds
95% ethyl alcohol for 30 seconds
EA stain for 3 minutes
95% ethyl alcohol for 1 minute
95% ethyl alcohol for 1 minute
95% ethyl alcohol for 1 minute
95% ethyl alcohol for 1 minute
Xylene for 1 minute
Xylene for 1 minute.

The reagents used to prepare or stain the cells adhering to the cell collection substrate may be purchased from any major biological supply house, for example OG-6, Modified EA-50 and Hematoxylin may be obtained from Surgipath Medical Industries, Inc., Grayslake, Ill. Alcohol and xylene may be obtained from any major industrial chemical supply house. Scott's tap water is made from normal tap water treated with magnesium sulfate and sodium bicarbonate (both available from Fisher Scientific or Mallinckrodt Corporation).

The membrane is removed from the device, placed flat on a microscope slide, and allowed to dry. The slide is flooded with chloroform to dissolve the nitrocellulose membrane, leaving the cells adhering to the slide.

Alternatively, the cell collection substrate is removed from the device, placed on a microscope glass slide (specimen side up) and clipped to the slide. Staining is performed as described above. After the last alcohol treatment, the substrate is mounted flat on a clean glass microscope slide using the mounting medium Clearium TM (Surgipath Corp.) and a coverslip is applied the Specimen is observed by a cytotechnologist or pathologist.

EXAMPLE 4

Processing of a Sample Collected on Polycarbonate

A sample is collected as described in Example 2, however, a polycarbonate membrane is used in place of the nitrocellulose filter. After fixing the cells, the device with membrane in place is immersed in reagent baths as described in Example 3. The polycarbonate membrane is then removed from the support member and placed on a microscope slide which has been previously sprayed with a transparent adhesive. A coverslip is then adhered to the slide using Clearium TM or another mounting medium. The cell specimen is then observed under a microscope.

Gynecologically imprinted substrates that are suitably stained show discrete cells in a monolayer, a highly desirable slide to examine compared to clumped cells in multiple layers. Representative cells from the transformation zone of the cervix are important to view as this area is that which is most prone to abnormal and malignant change. Therefore it is desirable to have a monolayer of cells from the transformation zone for the ideal cytological sample. The impression cytology technique described here provides an excellent distribution of cells from the transformation zone. Both of these features are superior to routine pap smears that are taken by cotton swabs, wood spatulas or brushes. Because of the improved cell representation provided by this technique, compared to routine pap tests, the number of false negative results is reduced.

We claim:

1. A device for obtaining cell samples suitable for microscopic examination directly from a human female reproductive tract, comprising:
   a means for collecting cells such that the cells adhere to the collection means as discrete cells in monolayer form; and
   a support means for holding said means for collecting cells.

2. The device of claim 1 further comprising a grasping means.

3. The device of claim 1 wherein the cell collection means comprises a polycarbonate membrane.

4. The device of claim 1 wherein the cell collection means comprises a cellulose acetate membrane.

5. The device of claim 1 wherein the cell collection means comprises a nitrocellulose membrane.

6. The device of claim 1 wherein the cell collection means comprises a glass fiber membrane.

7. The device of claim 1 wherein the support means comprises a rigid plastic material.

8. The device of claim 1 wherein the support means comprises a conical portion for holding said cell collection means.

9. The device of claim 1 wherein the support means comprises a cylindrical portion for holding said cell collection means.

10. The device of claim 1 wherein the support means comprises a flat portion for holding said cell collection means.

11. The device of claim 1 wherein the support means comprises a curved portion for holding said cell collection means.

12. The device of claim 1 wherein the cell collection means is a membrane impregnated with a selective binding agent.

13. The device of claim 12 wherein the selective binding agent is selected from the group consisting of antibodies, antigens and lectins.

14. The device of claim 12 wherein the selective binding agent is an antibody specific for an antigen of a pathogenic organism.

15. The device of claim 12 wherein the selective binding agent is an antibody specific for a tumor-associated antigen.

16. The device of claim 12 wherein a plurality of specific binding agents are impregnated into the cell collection means at different locations on the cell collection means.

17. A method of directly obtaining cell samples suitable for microscopic examination from a human female reproductive tract, comprising:
    contacting a human female reproductive tract with a cell collection means held by a support means to adhere cells from the human female reproductive tract to the cell collection means as discrete cells in a monolayer form;
    fixing the cells which adhere to the cell collection means on the cell collection means.

18. The method of claim 17 wherein the cell collection means is contacted with a cervical-endocervical transformation zone.

19. The method of claim 17 further comprising:
    adhering the cell collection means to a microscope slide.

20. The method of claim 19 wherein the step of adhering employs an adhesive selected from the group consisting of: one-part adhesives, two-part adhesives, and pressure sensitive adhesives.

21. The method of claim 19 further comprising treating said cell collection means to render said cell collection means transparent to visible light.

22. A device for obtaining cell samples suitable for microscopic examination directly from a human female reproductive tract, comprising:
    a membrane for collecting cells such that the cells adhere to the collection means as discrete cells in monolayer form; and
    a support means for holding said membrane in a conical configuration.

23. A method of directly obtaining cell samples suitable for microscopic examination from a human female reproductive tract, comprising:
    contacting a human female reproductive tract with a membrane held by a conical support to adhere cells from the human female cervical-endocervical transformation zone to the membrane as discrete cells in a monolayer form;
    fixing the cells which adhere to the membrane on the membrane;
    adhering the membrane to a microscope slide; and
    treating the membrane to render it transparent to visible light.

* * * * *